(12) United States Patent
Liu et al.

(10) Patent No.: US 11,703,557 B2
(45) Date of Patent: *Jul. 18, 2023

(54) SYSTEMS AND METHODS FOR ACTUAL GRADIENT WAVEFORM ESTIMATION

(71) Applicant: SHANGHAI UNITED IMAGING HEALTHCARE CO., LTD., Shanghai (CN)

(72) Inventors: Qi Liu, Houston, TX (US); Yuan Zheng, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/811,873

(22) Filed: Jul. 11, 2022

(65) Prior Publication Data

US 2022/0349969 A1 Nov. 3, 2022

Related U.S. Application Data

(63) Continuation of application No. 17/243,587, filed on Apr. 29, 2021, now Pat. No. 11,385,309.

(51) Int. Cl.
*G01R 33/385* (2006.01)
*A61B 5/055* (2006.01)
*G01R 33/56* (2006.01)
*G01R 33/54* (2006.01)
*G01R 33/36* (2006.01)

(52) U.S. Cl.
CPC .......... *G01R 33/3852* (2013.01); *A61B 5/055* (2013.01); *G01R 33/546* (2013.01); *G01R 33/5608* (2013.01); *G01R 33/3692* (2013.01)

(58) Field of Classification Search
CPC .......... G01R 33/3692; G01R 33/3852; G01R 33/5466; G01R 33/5608; A61B 5/055
See application file for complete search history.

(56) References Cited

U.S. PATENT DOCUMENTS

2008/0100292 A1 5/2008 Hancu
2018/0203081 A1 7/2018 Cohen et al.
2020/0300957 A1 9/2020 Chen et al.

OTHER PUBLICATIONS

D. H. Kim et al., Simple Analytic Variable-Density Spiral Design, Magnetic Resonance in Medicine, 2010, 1 page.
Jeff H. Duyn, et al., Simple Correction Method for k-Space Trajectory Deviations in MRI, Journal of Magnetic Resonance, 132: 150-153, 1998.
Nil Okai Addy et al., Simple Method for MR Gradient System Characterization and k-Space Trajectory Estimation, Magnetic Resonance in Medicine, 68: 120-129, 2012.
(Continued)

*Primary Examiner* — Gregory H Curran
(74) *Attorney, Agent, or Firm* — Metis IP LLC

(57) ABSTRACT

The present disclosure provides a system for MRI. The system may obtain MRI scan data of a subject by directing an MRI scanner to perform an MRI scan on the subject according to a first gradient waveform. The system may also determine a second gradient waveform based on the first gradient waveform and a gradient waveform determination model. The gradient waveform determination model may have been trained according to a machine learning algorithm. The system may further generate a target reconstruction image of the subject based on the second gradient waveform and the MRI scan data.

20 Claims, 12 Drawing Sheets

(56) References Cited

OTHER PUBLICATIONS

Ryan K. Robison et al., Fast, Simple Gradient Delay Estimation for Spiral MRI, Magnetic Resonance in Medicine, 63: 1683-1690, 2010.

Ryan K. Robison et al., Correction of $B_o$ eddy current effects in spiral MRI, Magnetic Resonance in Medicine, 81: 2501-2513, 2018.

500

```
┌─────────────────────────────────────────────────────────┐
│ Obtaining MRI scan data of a subject by directing an MRI │  510
│ scanner to perform an MRI scan on the subject according  │
│            to a first gradient waveform                  │
└─────────────────────────────────────────────────────────┘
                            │
                            ▼
┌─────────────────────────────────────────────────────────┐
│ Determining, based on the first gradient waveform and a  │
│   gradient waveform determination model, a second        │  520
│ gradient waveform, the gradient waveform determination   │
│   model having been trained according to a machine       │
│                   learning algorithm                     │
└─────────────────────────────────────────────────────────┘
                            │
                            ▼
┌─────────────────────────────────────────────────────────┐
│ Generating, based on the second gradient waveform and    │  530
│  the MRI scan data, a target reconstruction image of the │
│                         subject                          │
└─────────────────────────────────────────────────────────┘
```

┌──────────────────────────────────────────────────────────┐
│ Determining a preliminary gradient waveform by           │  610
│ processing the first gradient waveform using at least one│
│ response function                                        │
└──────────────────────────────────────────────────────────┘
                              │
                              ▼
┌──────────────────────────────────────────────────────────┐
│ Determining the second gradient waveform based on the    │  620
│ preliminary gradient waveform and the gradient waveform  │
│ determination model                                      │
└──────────────────────────────────────────────────────────┘

Obtaining a plurality of first training samples, each of the plurality of first training samples including sample first amplitude information of a sample first gradient waveform planned to be applied to a sample subject during a sample MRI scan and ground truth amplitude information of a ground truth gradient waveform applied to the sample subject during the sample MRI scan — 810

Obtaining a first preliminary model — 820

For each of the plurality of first training samples, generating sample preliminary amplitude information of the sample first gradient waveform of the first training sample using the amplitude response function — 830

Generating the amplitude determination model by training the first preliminary model using the sample preliminary amplitude information and the ground truth amplitude information of each of the plurality of first training samples — 840

1010 — Obtaining a plurality of second training samples, each of the plurality of second training samples including sample first phase information of a sample first gradient waveform planned to be applied to a sample subject during a sample MRI scan and ground truth phase information of a ground truth gradient waveform applied to the sample subject during the sample MRI scan

1020 — Obtaining a second preliminary model

1030 — For each of the plurality of second training samples, generating sample preliminary phase information of the sample first gradient waveform of the second training sample using the phase response function

1040 — Generating the phase determination model by training the second preliminary model using the sample preliminary phase information and the ground truth phase information of each of the plurality of second training samples

```
┌─────────────────────────────────────────────────┐
│ Obtaining a plurality of third training samples,│
│ each of the plurality of third training samples │
│ comprising sample preset amplitude information  │ 1110
│ and sample preset phase information of a sample │
│ preset gradient waveform planned to be applied  │
│ to a sample subject during a sample MRI scan,   │
│ and ground truth amplitude information and      │
│ ground truth phase information of a ground      │
│ truth gradient waveform applied to the sample   │
│ subject during the sample MRI scan              │
└─────────────────────────────────────────────────┘
                        │
                        ▼
┌─────────────────────────────────────────────────┐
│ Obtaining a third preliminary model comprising  │ 1120
│ a first sub-model and a second sub-model        │
└─────────────────────────────────────────────────┘
                        │
                        ▼
┌─────────────────────────────────────────────────┐
│ Generating a trained hybrid model by training   │ 1130
│ the third preliminary model using the plurality │
│ of third training samples                       │
└─────────────────────────────────────────────────┘
                        │
                        ▼
┌─────────────────────────────────────────────────┐
│ Designating the trained first sub-model of the  │ 1140
│ trained hybrid model as the amplitude           │
│ determination model                             │
└─────────────────────────────────────────────────┘
                        │
                        ▼
┌─────────────────────────────────────────────────┐
│ Designating the trained second sub-model of the │ 1150
│ trained hybrid model as the phase determination │
│ model                                           │
└─────────────────────────────────────────────────┘
```

```
┌─────────────────────────────────────────────────────────┐
│ Obtaining a first gradient waveform planned to be applied│  1210
│            to a subject during an MRI scan              │
└─────────────────────────────────────────────────────────┘
                            │
                            ▼
┌─────────────────────────────────────────────────────────┐
│ Determining, based on the first gradient waveform and a │
│    gradient waveform determination model, a second      │  1220
│ gradient waveform, the gradient waveform determination  │
│   model having been trained according to a machine      │
│                   learning algorithm                    │
└─────────────────────────────────────────────────────────┘
                            │
                            ▼
┌─────────────────────────────────────────────────────────┐
│  Directing, based on the second gradient waveform, an   │  1230
│   MRI scanner to perform the MRI scan on the subject    │
└─────────────────────────────────────────────────────────┘
```

FIG. 12

SYSTEMS AND METHODS FOR ACTUAL GRADIENT WAVEFORM ESTIMATION

CROSS-REFERENCE TO RELATED APPLICATIONS

This application is a continuation of U.S. patent application Ser. No. 17/243,587, filed on Apr. 29, 2021, the contents of each of which are hereby incorporated by reference.

TECHNICAL FIELD

The present disclosure generally relates to magnetic resonance imaging (MRI), and more particularly, systems and methods for actual gradient waveform estimation in MRI.

BACKGROUND

MRI systems have been widely employed in disease diagnosis and/or treatment. Normally, during an MRI scan (e.g., an ultra-short echo scan, a spiral MRI scan) of a subject, an actual gradient waveform applied to the subject may be different from a preset gradient waveform planned to be applied to the subject due to, for example, hardware limitations. The deviation of the actual gradient waveform with respect to the preset gradient waveform may affect the quality of a resulting image of the MRI scan. An approach to eliminate or reduce the effect of the deviation is to determine or estimate the actual gradient waveform, and perform image reconstruction based on the actual gradient waveform. Therefore, it is desirable to develop systems and methods for estimating an actual gradient waveform.

SUMMARY

According to an aspect of the present disclosure, a system for MRI is provided. The system may include at least one storage device including a set of instructions for MRI and at least one processor configured to communicate with the at least one storage device. When executing the set of instructions, the at least one processor may be configured to direct the system to perform operations. The system may obtain MRI scan data of a subject by directing an MRI scanner to perform an MRI scan on the subject according to a first gradient waveform. The system may determine a second gradient waveform based on the first gradient waveform and a gradient waveform determination model. The gradient waveform determination model may have been trained according to a machine learning algorithm. The system may generate a target reconstruction image of the subject based on the second gradient waveform and the MRI scan data.

In some embodiments, the determining a second gradient waveform based on the first gradient waveform and a gradient waveform determination model may comprise determining a preliminary gradient waveform by processing the first gradient waveform using at least one response function, and determining the second gradient waveform based on the preliminary gradient waveform and the gradient waveform determination model.

In some embodiments, the at least one response function may include an amplitude response function and a phase response function. The determining a preliminary gradient waveform by processing the first gradient waveform using at least one response function may comprise determining preliminary amplitude information of the preliminary gradient waveform by processing first amplitude information of the first gradient waveform using the amplitude response function, and determining preliminary phase information of the preliminary gradient waveform by processing first phase information of the first gradient waveform using the phase response function.

In some embodiments, the gradient waveform determination model may comprise an amplitude determination model and a phase determination model. The determining the second gradient waveform MRI based on the preliminary gradient waveform and the gradient waveform determination model may comprise determining second amplitude information of the second gradient waveform by processing the preliminary amplitude information using the amplitude determination model, and determining second phase information of the second gradient waveform by processing the preliminary amplitude information using the amplitude determination model.

In some embodiments, the amplitude determination model may be trained according to a first model training process. The first model training process may include obtaining a plurality of first training samples, obtaining a first preliminary model, and generating the amplitude determination model by training the first preliminary model using the plurality of first training samples. Each of the plurality of first training samples may comprise sample first amplitude information of a sample first gradient waveform planned to be applied to a sample subject during a sample MRI scan, and ground truth amplitude information of a ground truth gradient waveform applied to the sample subject during the sample MRI scan.

In some embodiments, the generating the amplitude determination model by training the first preliminary model using the plurality of first training samples may comprise: for each of the plurality of first training samples, generating sample preliminary amplitude information of the sample first gradient waveform of the first training sample using the amplitude response function; and generating the amplitude determination model by training the first preliminary model using the sample preliminary amplitude information and the ground truth amplitude information of each of the plurality of first training samples.

In some embodiments, the phase determination model may be trained according to a second model training process. The second model training process may include obtaining a plurality of second training samples, obtaining a second preliminary model, and generating the phase determination model by training the second preliminary model using the plurality of second training samples. Each of the plurality of second training samples may comprise sample first phase information of a sample first gradient waveform planned to be applied to a sample subject during a sample MRI scan, and ground truth phase information of a ground truth gradient waveform applied to the sample subject during the sample MRI scan.

In some embodiments, the generating the phase determination model by training the second preliminary model using the plurality of second training samples may comprise: for each of the plurality of second training samples, generating sample preliminary phase information of the sample first gradient waveform of the second training sample using the phase response function; and generating the phase determination model by training the second preliminary model using the sample preliminary phase information and the ground truth phase information of each of the plurality of second training samples.

In some embodiments, the amplitude determination model and the phase determination model are jointly trained according to a third model training process. The third model training process may include obtaining a plurality of third training samples; generating a trained hybrid model by training a third preliminary model that includes a first sub-model and a second sub-model using the plurality of third training samples; and designating the trained first sub-model and the trained second sub-model of the trained hybrid model as the amplitude determination model and the phase determination model, respectively. Each of the plurality of third training samples may comprise sample first amplitude information and sample first phase information of a sample first gradient waveform planned to be applied to a sample subject during a sample MRI scan, and ground truth amplitude information and ground truth phase information of a ground truth gradient waveform applied to the sample subject during the sample MRI scan.

In some embodiments, the amplitude determination model and the phase determination model may be convolutional neural network models.

In some embodiments, the MRI scan may be an ultrashort echo-time MRI scan or a spiral MRI scan.

According to another aspect of the present discourse, a system is provided. The system may include at least one storage device storing a set of instructions for MRI and at least one processor configured to communicate with the at least one storage device. When executing the set of instructions, the at least one processor may be configured to direct the system to perform operations. The system may obtain a first gradient waveform planned to be applied to a subject during an MRI scan. The system may determine a second gradient waveform, the gradient waveform determination model having been trained according to a machine learning algorithm based on the first gradient waveform and a gradient waveform determination model. The system may direct an MRI scanner to perform the MRI scan on the subject based on the second gradient waveform.

In some embodiments, the directing an MRI scanner to perform the MRI scan on the subject based on the second gradient waveform comprises determining an adjusted gradient waveform by adjusting the first gradient waveform according to the second gradient waveform, and directing the MRI scanner to perform the MRI scan on the subject according to the adjusted gradient waveform.

In some embodiments, the amplitude determination model and the phase determination model may be trained separately or jointly.

In some embodiments, the amplitude determination model and the phase determination model may be convolutional neural network models.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 5 is a flowchart illustrating an exemplary process for generating a target reconstruction image of a subject according to some embodiments of the present disclosure;

FIG. 6 is a flowchart illustrating an exemplary process for determining a second gradient waveform based on a first gradient waveform and a gradient waveform determination model according to some embodiments of the present disclosure;

FIG. 8 is a flowchart illustrating an exemplary process for generating an amplitude determination model according to some embodiments of the present disclosure;

FIG. 10 is a flowchart illustrating an exemplary process for generating a phase determination model according to some embodiments of the present disclosure;

FIG. 11 is a flowchart illustrating an exemplary process for jointly generating an amplitude determination model and a phase determination model according to some embodiments of the present disclosure; and FIG. 12 is a flowchart illustrating an exemplary process for performing an MRI scan on a subject according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

Figure 2:
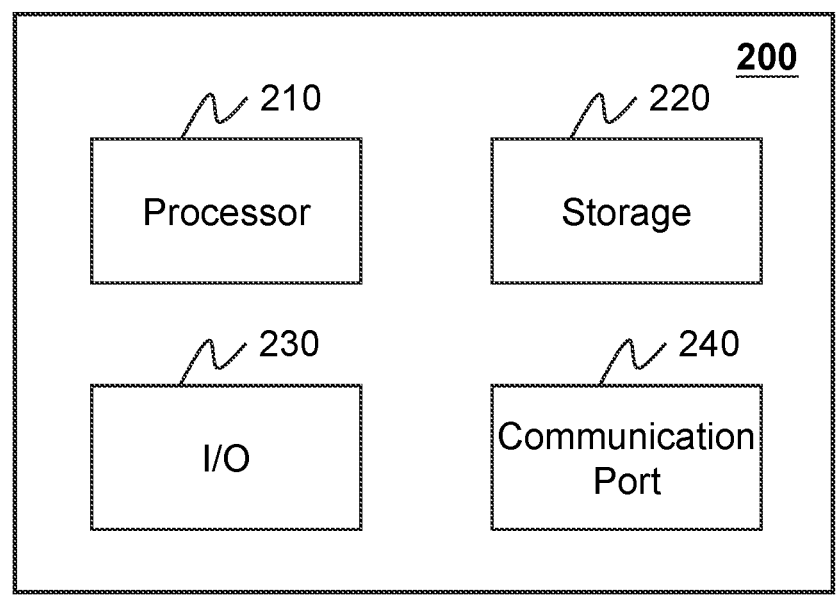
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging and/or treatment, such as for disease diagnosis, treatment or research purposes. In some embodiments, the systems may include a radiotherapy (RT) system, a computed tomography (CT) system, an emission computed tomography (ECT) system, an X-ray photography system, a positron emission tomography (PET) system, or the like, or any combination thereof. For illustration purposes, the disclosure describes systems and methods for radiotherapy.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, an organ of a subject, or any combination thereof, which may be displayed in an image (e.g., a planning image, or a treatment image, etc.) and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

An MRI scan is often performed on a subject to collect MRI scan data of the subject for disease diagnosis and/or treatment. However, due to hardware limitations (e.g., an RF amplifier, a gradient delay, an eddy) of an MRI scanner, an actual gradient waveform applied to the subject may be different from a preset gradient waveform planned to be applied to the subject. An MRI image may have a poor image quality (e.g., include artifacts) if it is reconstructed based on the preset gradient waveform. Conventionally, it is often assumed that the gradient system of the MRI scanner fits a linear model, and the linear model is used to predict the actual gradient waveform. However, non-linear factors, such as a non-linear effect of the power amplifier, a non-linear turbulence, or the like, or any combination thereof, may be omitted by the conventional approach. The actual gradient waveform prediction using the linear model may have limited accuracy (e.g., result in image artifacts), especially when a gradient field changes rapidly during the MRI scan.

An aspect of the present disclosure relates to systems and methods for actual gradient waveform estimation in MRI. The systems and methods may obtain MRI scan data of a subject by directing an MRI scanner to perform an MRI scan on the subject according to a first gradient waveform (or referred to as a preset gradient waveform or an ideal gradient waveform). The systems and methods may determine a second gradient waveform based on the first gradient waveform and a gradient waveform determination model. The gradient waveform determination model may be trained according to a machine learning algorithm. The second gradient waveform may be regarded as an estimation value of an actual gradient waveform that is actually applied to the subject during the MRI scan. The systems and methods may further generate a target reconstruction image of the subject based on the second gradient waveform and the MRI scan data.

In some embodiments, the systems and methods may perform actual gradient waveform estimation before an MRI scan, and implement the MRI scan based on the determination result. Specifically, the systems and methods may obtain the first gradient waveform planned to be applied to the subject. The systems and methods may also determine the second gradient waveform based on the first gradient waveform and the gradient waveform determination model. The systems and methods may further determine an adjusted gradient waveform by adjusting the first gradient waveform according to the second gradient waveform, and direct an MRI scanner to perform the MRI scan on the subject according to the adjusted gradient waveform.

According to some embodiments of the present disclosure, the gradient waveform determination model may be used to determine the second gradient waveform so as to estimate the actual gradient waveform. Compared with a conventional liner model, the gradient waveform determination model, which learns an optimal mechanism for predicting the second gradient waveform from training data, may have improved accuracy. The gradient waveform determination model may take linear factors, non-linear factors, as well as complex factors (which are usually undetectable by human or traditional actual gradient waveform determination approaches) into consideration. The application of the gradient waveform determination model may improve the accuracy of the determined second gradient waveform, which in turn, the accuracy of the image reconstruction performed based on the second gradient waveform or the MRI scan performed based on the second gradient waveform.

Figure 1:
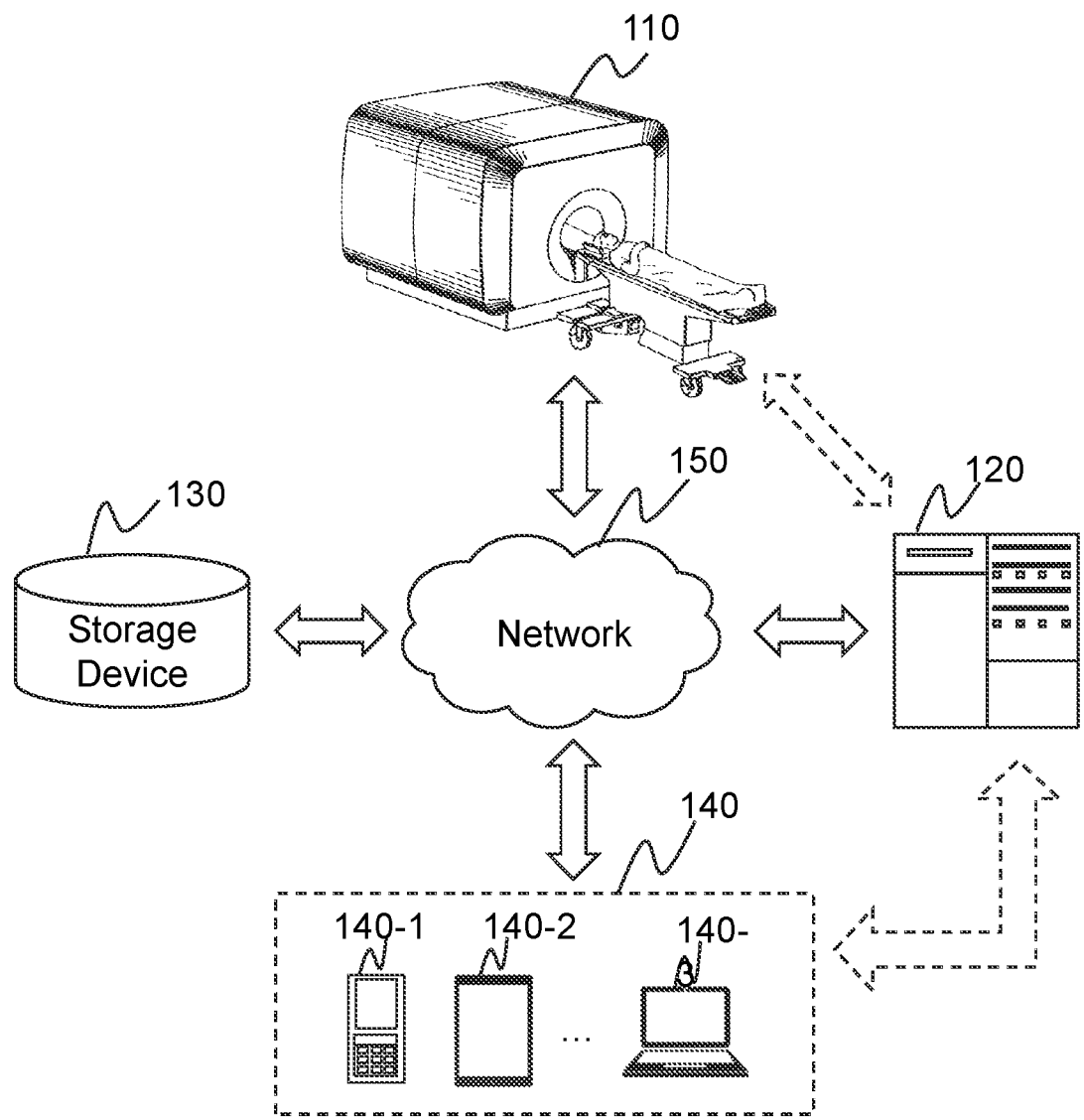
FIG. 1 is a schematic diagram illustrating an exemplary MRI system according to some embodiments of the present disclosure.

FIG. 1 is a schematic diagram illustrating an exemplary MRI system 100 according to some embodiments of the present disclosure. As shown in FIG. 1, the MRI system 100 may include an MRI scanner 110, a processing device 120, a storage device 130, one or more terminals 140, and a network 150. In some embodiments, the MRI scanner 110, the processing device 120, the storage device 130, and/or the terminal(s) 140 may be connected to and/or communicate with each other via a wireless connection, a wired connection, or a combination thereof. The connections between the components in the MRI system 100 may be variable. For example, the MRI scanner 110 may be connected to the processing device 120 through the network 150. As another example, the MRI scanner 110 may be connected to the processing device 120 directly.

The MRI scanner 110 may be configured to scan a subject (or a part of the subject) to acquire image data, such as echo signals (or MRI signals) associated with the subject. In some embodiments, the MRI scanner 110 may include, for example, a main magnet, a gradient coil (or also referred to as a spatial encoding coil), a radio frequency (RF) coil, etc.

In some embodiments, the MRI scanner 110 may include a gradient coil configured to apply a preset gradient waveform to the subject. However, due to equipment limitations, an actual gradient waveform applied to the subject during the MRI scan may be different from the preset gradient waveform. In some embodiments, the MRI scanner 110 may be a permanent magnet MRI scanner, a superconducting electromagnet MRI scanner, or a resistive electromagnet MRI scanner, etc., according to the type of the main magnet. In some embodiments, the MRI scanner 110 may be a high-field MRI scanner, a mid-field MRI scanner, and a low-field MRI scanner, etc., according to the intensity of the magnetic field.

The subject scanned by the MRI scanner 110 may be biological or non-biological. For example, the subject may include a patient, a man-made object, etc. As another example, the subject may include a specific portion, organ, tissue, and/or a physical point of the patient. Merely by way of example, the subject may include head, brain, neck, body, shoulder, arm, thorax, cardiac, stomach, blood vessel, soft tissue, knee, feet, or the like, or a combination thereof.

The processing device 120 may process data and/or information obtained from the MRI scanner 110, the storage device 130, and/or the terminal(s) 140. For example, the processing device 120 may determine a second gradient waveform (i.e., an estimated actual gradient waveform) by applying a gradient waveform determination model. As another example, the processing device 120 may generate the gradient waveform determination model by model training.

In some embodiments, a trained model (e.g., an amplitude determination model and/or a phase determination model) may be generated by a processing device, while the application of the trained model may be performed on a different processing device. In some embodiments, the trained model may be generated by a processing device of a system different from the MRI system 100 or a server different from the processing device 120 on which the application of the trained model is performed. For instance, the trained model may be generated by a first system of a vendor who provides and/or maintains such a trained model, while actual gradient waveform estimation based on the provided trained model may be performed on a second system of a client of the vendor. In some embodiments, the application of the trained model may be performed online in response to a request for determining a second gradient waveform. In some embodiments, the trained model may be determined or generated offline.

In some embodiments, the trained model may be determined and/or updated (or maintained) by, e.g., the manufacturer of the MRI scanner 110 or a vendor. For instance, the manufacturer or the vendor may load the amplitude determination model and/or the phase determination model into the MRI system 100 or a portion thereof (e.g., the processing device 120) before or during the installation of the MRI scanner 110 and/or the processing device 120, and maintain or update the amplitude determination model and/or the phase determination model from time to time (periodically or not). The maintenance or update may be achieved by installing a program stored on a storage device (e.g., a compact disc, a USB drive, etc.) or retrieved from an external source (e.g., a server maintained by the manufacturer or vendor) via the network 150. The program may include a new model (e.g., a newly trained model) or a portion of a model that substitutes or supplements a corresponding portion of the model.

In some embodiments, the processing device 120 may be a single server or a server group. The server group may be centralized or distributed. In some embodiments, the processing device 120 may be local or remote. For example, the processing device 120 may access information and/or data from the MRI scanner 110, the storage device 130, and/or the terminal(s) 140 via the network 150. As another example, the processing device 120 may be directly connected to the MRI scanner 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 200 having one or more components as described in connection with FIG. 2.

The storage device 130 may store data, instructions, and/or any other information. In some embodiments, the storage device 130 may store data obtained from the MRI scanner 110, the processing device 120, and/or the terminal(s) 140. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or a combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the MRI system 100 (e.g., the MRI scanner 110, the processing device 120, and/or the terminal(s) 140). One or more components of the MRI system 100 may access the data or instructions stored in the storage device 130 via the network 150. In some embodiments, the storage device 130 may be part of the processing device 120 or the terminal(s) 140.

The terminal(s) 140 may be configured to enable a user interaction between a user and the MRI system 100. For example, the terminal(s) 140 may receive an instruction to cause the MRI scanner 110 to scan the subject from the user. As another example, the terminal(s) 140 may receive a processing result (e.g., a slice image representative of a slice location of the subject) from the processing device 120 and display the processing result to the user. In some embodiments, the terminal(s) 140 may be connected to and/or communicate with the MRI scanner 110, the processing device 120, and/or the storage device 130. In some embodiments, the terminal(s) 140 may include a mobile device 140-1, a tablet computer 140-2, a laptop computer 140-3, or the like, or a combination thereof. For example, the mobile device 140-1 may include a mobile phone, a personal digital assistant (PDA), a gaming device, a navigation device, a point of sale (POS) device, a laptop, a tablet computer, a desktop, or the like, or a combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120 or the MRI scanner 110.

The network 150 may include any suitable network that can facilitate the exchange of information and/or data for the MRI system 100. In some embodiments, one or more components of the MRI system 100 (e.g., the MRI scanner 110, the processing device 120, the storage device 130, the terminal(s) 140, etc.) may communicate information and/or data with one or more other components of the MRI system 100 via the network 150. For example, the processing device 120 may obtain image data (e.g., an echo signal) from the MRI scanner 110 via the network 150. As another example, the processing device 120 may obtain user instructions from the terminal(s) 140 via the network 150. The network 150 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, or the like, or a combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 150 may include one or more network access points. For example, the network 150 may include wired and/or wireless network access points such as base stations and/or internet exchange points through which one or more components of the MRI system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. In some embodiments, the MRI system 100 may include one or more additional components and/or one or more components described above may be omitted. Additionally or alternatively, two or more components of the MRI system 100 may be integrated into a single component. For example, the processing device 120 may be integrated into the MRI scanner 110. As another example, a component of the MRI system 100 may be replaced by another component that can implement the functions of the component. In some embodiments, the storage device 130 may be a data storage including cloud computing platforms, such as a public cloud, a private cloud, a community and hybrid cloud, etc. However, those variations and modifications do not depart the scope of the present disclosure.

FIG. 2 is a schematic diagram illustrating exemplary hardware and/or software components of a computing device 200 according to some embodiments of the present disclosure. The computing device 200 may be used to implement any component of the MRI system 100 as described herein. For example, the processing device 120 and/or the terminal(s) 140 may be implemented on the computing device 200, respectively, via its hardware, software program, firmware, or a combination thereof. Although only one such computing device is shown, for convenience, the computer functions relating to the MRI system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process data obtained from the MRI scanner 110, the terminal(s) 140, the storage device 150, and/or any other component of the MRI system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data obtained from one or more components of the MRI system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure. For example, the storage device 220 may store a program for the processing device 120 to execute for generating a gradient waveform determination model.

The I/O 230 may input and/or output signals, data, information, etc. In some embodiments, the I/O 230 may enable a user interaction with the processing device 120. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 150) to facilitate data communications. The communication port 240 may establish connections between the processing device 120 and the MRI scanner 110, the terminal(s) 140, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
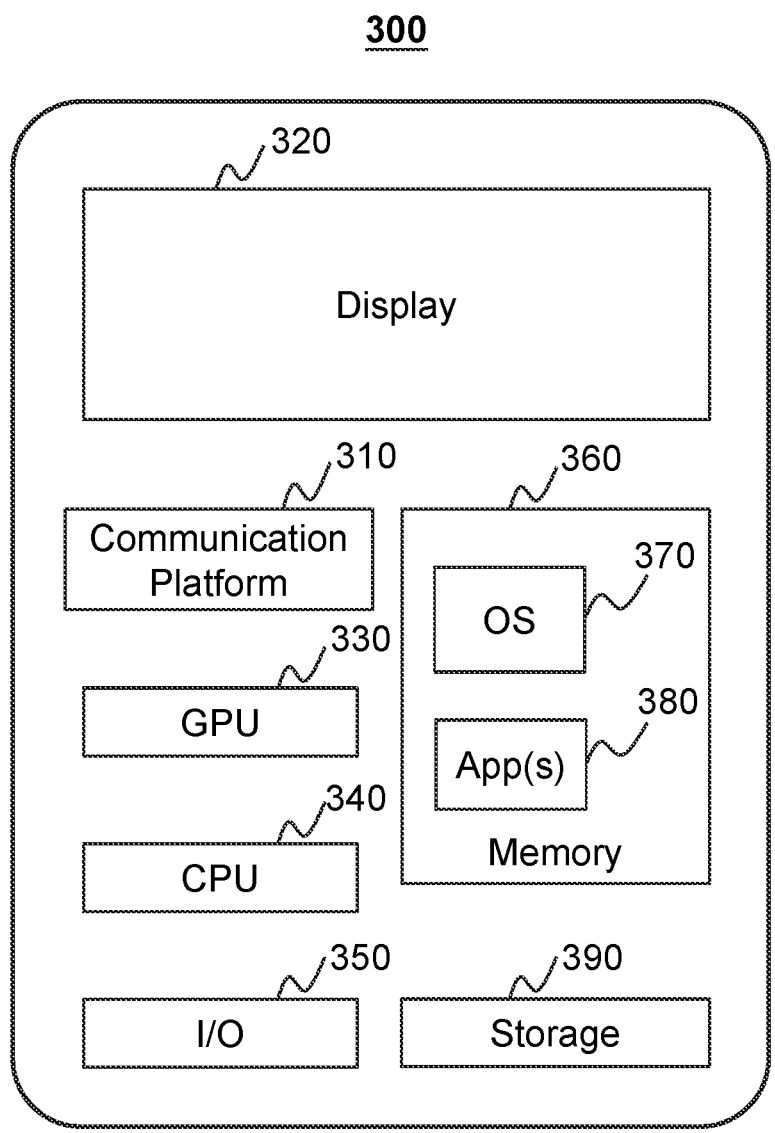
FIG. 3 is a schematic diagram illustrating exemplary hardware and/or software components of a mobile device according to some embodiments of the present disclosure.

FIG. 3 is a schematic diagram illustrating exemplary hardware and/or software components of an exemplary mobile device 300 according to some embodiments of the present disclosure. In some embodiments, a terminal 140 and/or a processing device 120 may be implemented on a mobile device 300, respectively. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™' Windows Phone™) and one or more applications 380 may be loaded into the memory 360 from the storage 390 in order to be executed by the CPU 340. The applications 380 may include a browser or any other suitable mobile apps for receiving and rendering information relating to the MRI system 100. User interactions with the information stream may be achieved via the I/O 350 and provided to the processing device 120 and/or other components of the MRI system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
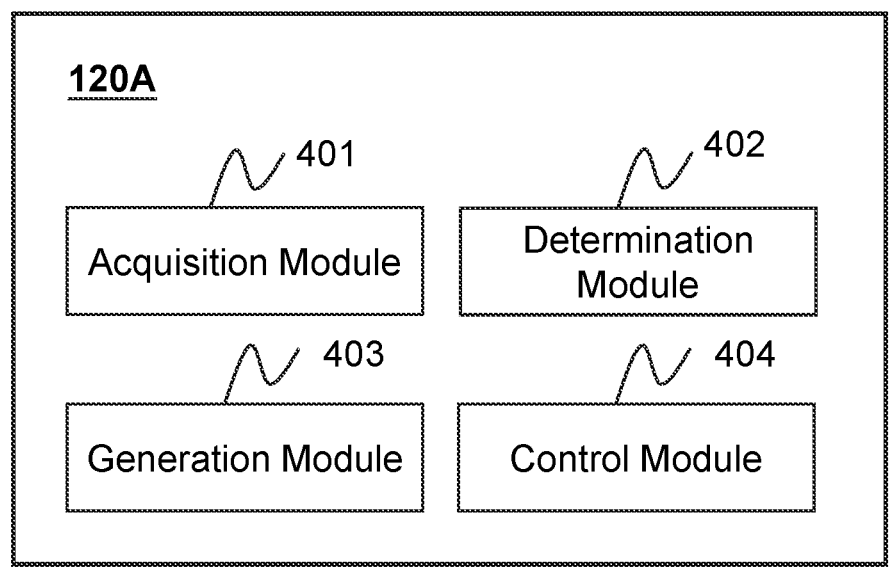
FIGS. 4A and 4B are block diagrams illustrating exemplary processing devices according to some embodiments of the present disclosure.
Figure 4B:
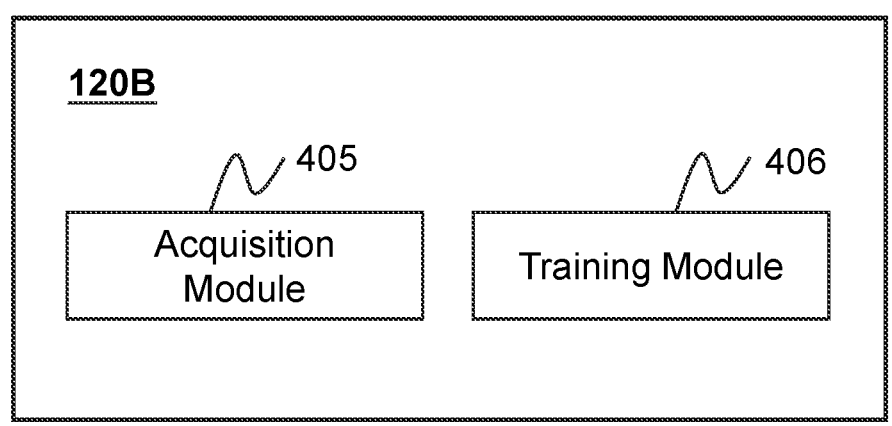

FIGS. 4A and 4B are block diagrams illustrating exemplary processing devices 120A and 120B according to some embodiments of the present disclosure. In some embodiments, the processing devices 120A and 120B may be embodiments of the processing device 120 as described in connection with FIG. 1. The processing device 120A may be configured to perform actual gradient waveform prediction by applying a gradient waveform determination model. The processing device 120B may be configured to generate the gradient waveform determination model by model training.

In some embodiments, the processing devices 120A and 120B may be respectively implemented on a processing unit (e.g., the processor 210 illustrated in FIG. 2 or the CPU 340 as illustrated in FIG. 3). Merely by way of example, the processing devices 120A may be implemented on a CPU 340 of a terminal device, and the processing devices 120B may be implemented on a computing device 200. As another example, the processing device 120A may be implemented on a computing device of the MRI system 100, while the processing device 120B may be part of a device or a system of the manufacturer of the MRI system 100, or a portion thereof (e.g., the MRI scanner 110). Alternatively, the processing devices 120A and 120B may be implemented on a same computing device 200 or a same CPU 340. For example, the processing devices 120A and 120B may be implemented on a same computing device 200.

As shown in FIG. 4A, the processing device 120A may include an acquisition module 401, a determination module 402, a generation module 403, and a control module 404.

The acquisition module 401 may be configured to obtain information relating to the MRI system 100. For example, the acquisition module 401 may obtain MRI scan data of a subject by directing an MRI scanner to perform an MRI scan of the subject according to a first gradient waveform. The first gradient waveform refers to a gradient waveform planned to be applied to the subject during the MRI scan. As another example, the acquisition module 401 may be configured to obtain the first gradient waveform planned to be applied to the subject before the MRI scan is performed.

The determination module 402 may be configured to determine a second gradient waveform based on the first gradient waveform and a gradient waveform determination model. The second gradient waveform may be an estimated value of an actual gradient waveform applied to the subject during the MRI scan. In some embodiments, the determination module 402 may be configured to determine a preliminary gradient waveform by processing the first gradient waveform using at least one response function. The determination module 402 may be configured to determine the second gradient waveform based on the preliminary gradient waveform and the gradient waveform determination model. More descriptions regarding the determination of the second gradient waveform may be found elsewhere in the present disclosure. See, e.g., operation 520 in FIG. 5 and relevant descriptions thereof. In some embodiments, the determination module 402 may be configured to determine an adjusted gradient waveform by adjusting the first gradient waveform according to the second gradient waveform. More descriptions regarding the determination of the adjusted gradient waveform may be found elsewhere in the present disclosure. See, e.g., operation 1230 in FIG. 12 and relevant descriptions thereof.

The generation module 403 may be configured to generate a target reconstruction image of the subject based on the second gradient waveform and the MRI scan data. More descriptions regarding the generation of the target reconstruction image may be found elsewhere in the present disclosure. See, e.g., operation 530 in FIG. 5 and relevant descriptions thereof.

The control module 404 may be configured to control one or more components of the MRI system 100. For example, the control module 404 may direct an MRI scanner to perform the MRI scan on the subject according to the adjusted gradient waveform.

As shown in FIG. 4B, the processing device 120B may include an acquisition module 405 and a training module 406.

The acquisition module 405 may be configured to obtain training data used in generating one or more trained models as disclosed herein, such as a gradient waveform determination model, an amplitude determination model, a phase determination model. For example, the acquisition module 405 may be configured to obtain a plurality of first training samples and a first preliminary model, which may be used to generate the amplitude determination model. As another example, the acquisition module 405 may be configured to obtain a plurality of second training samples and a second preliminary model, which may be used to generate the phase determination model. As yet another example, the acquisition module 405 may be configured to obtain a plurality of third training samples and a third preliminary model comprising a first sub-model and a second sub-model, which may be used to jointly generate the amplitude determination model and the phase determination model. More descriptions regarding the training data may be found elsewhere in the present disclosure. See, e.g., FIGS. 8-11 and relevant descriptions thereof.

The training module 406 may be configured to generate one or more trained models (e.g., machine learning models) by model training. In some embodiments, the one or more trained models may be generated according to a machine learning algorithm. The machine learning algorithm may include but not be limited to an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the one or more machine learning models may be a supervised learning algorithm, a semi-supervised learning algorithm, an unsupervised learning algorithm, or the like. More descriptions regarding the generation of the one or more trained models may be found elsewhere in the present disclosure. See, e.g., FIGS. 8-11 and relevant descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120A and the processing device 120B may share two or more of the modules, and any one of the modules may be divided into two or more units. For instance, the processing devices 120A and 120B may share a same acquisition module, that is, the acquisition module 401 and the acquisition module 405 are a same module. In some embodiments, the processing device 120A and/or the processing device 120B may include one or more additional modules, such as a storage module (not shown) for storing data. In some embodiments, the processing device 120A and the processing device 120B may be integrated into one processing device 120.

FIG. 5 is a flowchart illustrating an exemplary process for generating a target reconstruction image of a subject according to some embodiments of the present disclosure. In some embodiments, process 500 may be executed by the MRI system 100. For example, the process 500 may be implemented as a set of instructions (e.g., an application) stored in a storage device (e.g., the storage device 150, the storage device 220, and/or the storage 390). In some embodiments, the processing device 120A (e.g., the processor 210 of the computing device 200, the CPU 340 of the mobile device 300, and/or one or more modules illustrated in FIG. 4A) may execute the set of instructions, and when executing the instructions, the processing device 120A may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In 510, the processing device 120A (e.g., the acquisition module 401) may obtain MRI scan data of the subject by directing an MRI scanner to perform an MRI scan of the subject according to a first gradient waveform.

The subject may be biological or non-biological. For example, the subject may include a patient, a man-made object, etc. As another example, the subject may include a specific portion, organ, tissue, and/or a physical point of the patient. Merely by way of example, the subject may include head, brain, neck, body, shoulder, arm, thorax, cardiac, stomach, blood vessel, soft tissue, knee, feet, or the like, or a combination thereof.

In some embodiments, the processing device 120A may direct the MRI scanner (e.g., the MRI scanner 110) to perform the MRI scan on the subject according to the first gradient waveform, and obtain MRI scan data from the MRI scanner. Alternatively, the MRI scan data may be previously collected and stored in a storage device (e.g., the storage device 130, the storage device 220, an external storage device). The processing device 120A may retrieve the MRI scan data from the storage device. In some embodiments, the MRI scan may be an ultrashort echo-time MRI or a spiral MRI scan.

The first gradient waveform refers to a gradient waveform planned to be applied to the subject during the MRI scan. In some embodiments, the first gradient waveform may be defined by first amplitude information and first phase information of the first gradient waveform. For example, the first amplitude information may include an amplitude of the first gradient waveform at a plurality of time points. The first phase information may include a phase of the first gradient waveform at the plurality of time points. In some embodiments, the first amplitude information may be represented as a first vector, and the first phase information may be represented as a second vector.

In some embodiments, the first gradient waveform may be determined according to a default setting of the MRI system 100 or set manually by a user of the MRI system 100 via, e.g., a terminal (e.g., the terminal 140). For example, the first gradient waveform may be selected by a doctor from a plurality of first gradient waveforms. Alternatively, the first gradient waveform may be determined by the processing device 120A based on an actual condition. For example, the first gradient waveform may be determined by the processing device 120A based on information relating to the subject, such as the scan region, the age, the body shape, or the like, or any combination thereof, of the subject. In some embodiments, the processing device 120A may obtain one or more scanning parameters (e.g., a field of view, a bandwidth) according to which the MRI scan is planned to be performed. The processing device 120A may further determine the first gradient waveform based on the one or more scanning parameters.

In application, due to hardware limitations as described elsewhere in the present application, an actual gradient waveform applied to the subject may be different from the first gradient waveform. Image reconstruction using the first gradient waveform may result in an MRI image with low image quality (e.g., having artifacts). Therefore, a second gradient waveform, which is an estimated value of the actual gradient waveform, may need to be determined and used to reconstruct a target reconstruction image of the subject with improved image quality.

In 520, the processing device 120A (e.g., the determination module 402) may determine the second gradient waveform based on the first gradient waveform and a gradient waveform determination model.

In some embodiments, the second gradient waveform may be defined by second amplitude information and second phase information of the second gradient waveform. For example, the second amplitude information may include an amplitude of the second gradient waveform at a plurality of time points. The second phase information may include a phase of the second gradient waveform at the plurality of time points.

As used herein, a gradient waveform determination model refers to a trained model (e.g., a machine learning model) or an algorithm configured for determining information relating to a second gradient waveform based on its input. For example, the processing device 120A may input the first amplitude information and the first phase information of the first gradient waveform into the gradient waveform determination model, and the gradient waveform determination model may output the second amplitude information and the second phase information of the second gradient waveform. As another example, the processing device 120A may determine a preliminary gradient waveform based on the first gradient waveform and at least one response function. The processing device 120A may further input information of the preliminary gradient waveform into the gradient waveform determination model, and the gradient waveform determination model may output the second amplitude information and the second phase information of the second gradient waveform. More descriptions regarding the preliminary gradient waveform may be found elsewhere in the present disclosure. See, e.g., FIG. 6 and relevant descriptions thereof.

In some embodiments, the gradient waveform determination model may include an amplitude determination model and a phase determination model. An amplitude determination model refers to a trained model (e.g., a machine learning model) or an algorithm configured for determining second amplitude information of a second gradient waveform based on its input. A phase determination model refers to a trained model (e.g., a machine learning model) or an algorithm configured for determining second phase information of a second gradient waveform based on its input.

In some embodiments, the amplitude determination model and the phase determination model may be two independent models that are trained separately. In other words, the processing device 120A may obtain the two independent models, and determine the second gradient waveform based on the two independent models. For example, the processing device 120A may determine a first input of the amplitude determination model based on the first gradient waveform, and determine the second amplitude information of the second gradient waveform based on the first input and the amplitude determination model. The processing device 120A may also determine a second input of the phase determination model based on the first gradient waveform, and determine the second phase information of the second gradient waveform based on the second input and the phase determination model.

Alternatively, the amplitude determination model and the phase determination model may be two sub-models of a hybrid trained model, wherein the amplitude determination model and the phase determination model may be jointly trained during the generation process of the trained hybrid model. In other words, the processing device 120A may obtain a single trained hybrid model including the amplitude determination model and the phase determination model, and determine the second gradient waveform based on the trained hybrid model. For example, the processing device 120A may determine a third input of the trained hybrid model, and determine the second amplitude information and the second phase information of the second gradient waveform based on the trained hybrid model and the third input. For the convenience of descriptions, the present disclosure uses the term "gradient waveform determination model" to collectively refer to the phase determination model, the amplitude determination model, the trained hybrid model, or any combination of these models. More descriptions regarding the determination of the second gradient waveform based on the gradient waveform determination model may be found elsewhere in the present disclosure. See, e.g., FIG. 7 and relevant descriptions thereof.

In some embodiments, the gradient waveform determination model may be a machine learning model according to a machine learning algorithm. For example, the gradient waveform determination model may include a neural network model, such as a convolutional neural network (CNN) model (e.g., a full CNN model, V-net model, a U-net model, an AlexNet model, an Oxford Visual Geometry Group (VGG) model, a ResNet model), a generative adversarial network (GAN) model, or the like, or any combination thereof. In some embodiments, the gradient waveform determination model may include one or more components for feature extraction and/or feature combination, such as a fully convolutional block, a skip-connection, a residual block, a dense block, or the like, or any combination thereof.

Exemplary machine learning algorithms may include an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the gradient waveform determination model may be a supervised learning algorithm, a semi-supervised learning algorithm, an unsupervised learning algorithm, or the like.

In some embodiments, the processing device 120A may obtain the gradient waveform determination model from one or more components of the MRI system 100 (e.g., the storage device 130, the terminals(s) 140) or an external source via a network (e.g., the network 150). For example, the gradient waveform determination model may be previously trained by a computing device (e.g., the processing device 120B), and stored in a storage device (e.g., the storage device 130, the storage device 220, and/or the storage 390) of the MRI system 100. The processing device 120A may access the storage device and retrieve the gradient waveform determination model from the storage device. In some embodiments, the amplitude waveform determination model may be trained by a computing device (e.g., the processing device 120B) by performing process 800 disclosed herein. The phase generation model may be trained by a computing device (e.g., the processing device 120B) by performing process 1000 disclosed herein. The trained hybrid model may be trained by a computing device (e.g., the processing device 120B) by performing process 1100 disclosed herein. Different models may be trained by a same computing device or different computing devices.

In 530, the processing device 120A (e.g., the generation module 403) may generate the target reconstruction image of the subject based on the second gradient waveform and the MRI scan data.

In some embodiments, the processing device 120A may generate k-space data by filling the MRI scan data into K-space according to the second gradient waveform. The processing device 120A may further reconstruct the target reconstruction image of the subject based on the k-space data, for example, by performing an inverse Fourier transformation on the k-space data. In some embodiments, the processing device 120A may generate the target reconstruction image using an MRI image reconstruction algorithm.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. Merely by way of example, the process 500 may include an additional operation to transmit the target reconstruction image to a terminal for display. As another example, operation 530 may be omitted.

FIG. 6 is a flowchart illustrating an exemplary process for determining a second gradient waveform based on a first gradient waveform and a gradient waveform determination model according to some embodiments of the present disclosure. In some embodiments, the process 600 may be performed to achieve at least part of operation 520 as described in connection with FIG. 5.

In 610, the processing device 120A (e.g., the determination module 402) may determine a preliminary gradient waveform by processing the first gradient waveform using at least one response function.

As used herein, a response function may include a linear function or model that can be used for actual gradient waveform prediction. The at least one response function may take liner factors, such as a linear effect of a power amplifier, a linear effect of turbulence, or the like, or any combination thereof, into consideration in the actual gradient waveform prediction. However, non-linear factors, such as a non-linear effect of the power amplifier, a non-linear turbulence, or the like, or any combination thereof, may be omitted by the at least one response function. The actual gradient waveform prediction using the at least one response function may have limited accuracy (e.g., result in image artifact), especially when a gradient field changes rapidly during the MRI scan. Therefore, the present disclosure uses the at least one response function to pre-process the first gradient waveform to determine the preliminary gradient waveform, and further uses the gradient waveform determination model to determine the second gradient waveform based on the preliminary gradient waveform. In this way, both the linear factors and the non-linear factors may be taken into consideration, thereby improving the accuracy of the determined second gradient waveform, and in turn, the accuracy of image reconstruction performed based on the second gradient waveform. In addition, by pre-processing the first gradient waveform, the computation amount of the gradient waveform determination model may be reduced, which may improve the efficiency of the second gradient waveform determination.

The preliminary gradient waveform may be defined by preliminary amplitude information and preliminary phase information of the preliminary gradient waveform. For example, the preliminary amplitude information may include an amplitude of the preliminary gradient waveform a plurality of time points. The preliminary phase information may include a phase of the preliminary phase gradient waveform at the plurality of time points.

In some embodiments, the processing device 120A may input information relating to the first gradient waveform into the at least one response function, and the at least one response function may output information relating to the preliminary gradient waveform. For example, the at least one response function may include an amplitude response function and a phase response function. The processing device 120A may determine the preliminary phase information of the preliminary gradient waveform by processing the first phase information of the first gradient waveform using the phase response function. The processing device 120A may determine the preliminary amplitude information of the preliminary gradient waveform by processing the first amplitude information of the first gradient waveform using the amplitude response function.

In some embodiments, the at least one response function may be determined by the processing device 120A based on experimental data of one or more experimental scans (e.g., actual scans or simulated scans) performed on one or more experimental subjects. Alternatively, the at least one response function may be previously determined by the processing device 120A or another computing device, and stored in a storage device (e.g., the storage device 130, the storage device 220, and/or the storage 390). The processing device 120A may retrieve the at least one response function from the storage device.

In 620, the processing device 120A (e.g., the determination module 402) may determine the second gradient waveform based on the preliminary gradient waveform and the gradient waveform determination model.

In some embodiments, as described in connection with FIG. 5, the gradient waveform determination model may include an amplitude determination model and a phase determination model. The processing device 120A may determine the second amplitude information of the second gradient waveform by processing the preliminary amplitude information using the amplitude determination model. The processing device 120A may determine the second phase information of the second gradient waveform by processing the preliminary phase information using the phase determination model.

Figure 7:
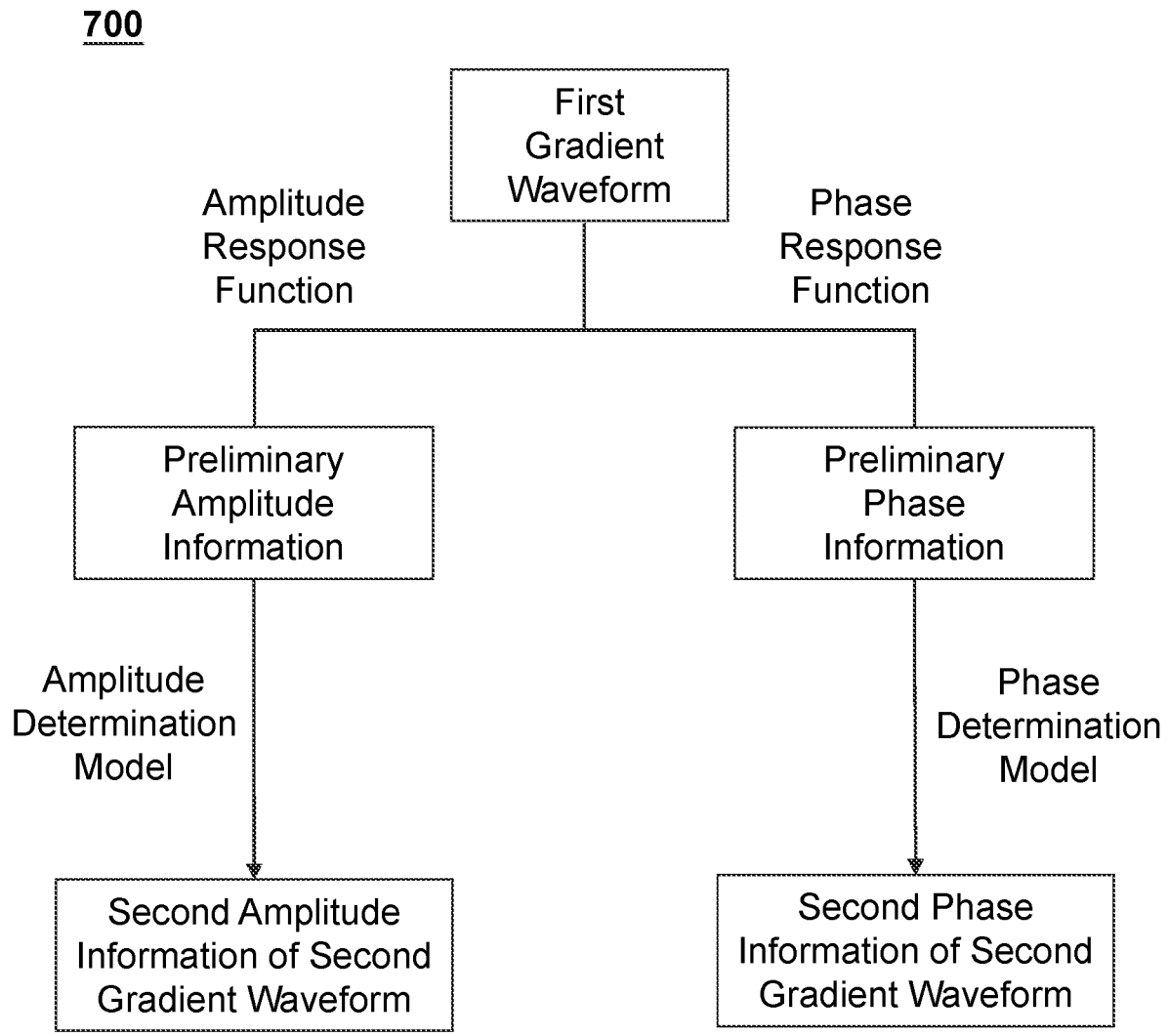
FIG. 7 is a schematic diagram illustrating an exemplary process for determining a second gradient waveform according to some embodiments of the present disclosure.

For illustration purposes, FIG. 7 illustrates a schematic diagram of an exemplary process for determining a second gradient waveform according to some embodiments of the present disclosure.

As shown in FIG. 7, the processing device 120A may process information of the first gradient waveform using the amplitude response function and the phase response function. For example, the first amplitude information of the first gradient waveform may be processed by the amplitude response function to determine the preliminary amplitude information of the preliminary gradient waveform. The first phase information of the first gradient waveform may be processed by the phase response function to determine the preliminary phase information of the preliminary gradient waveform.

Then, the processing device 120A may process the preliminary amplitude information using the amplitude determination model to determine the second amplitude information of the second gradient waveform. The processing device 120A may process the preliminary phase information using the phase determination model to determine the second phase information of the second gradient waveform.

It should be noted that the above descriptions regarding FIGS. 6 and 7 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120A may determine the second gradient waveform based on the gradient waveform determination model without using the at least one response function. For example, the second amplitude information of the second gradient waveform may be determined by processing the first amplitude information of the first gradient waveform using the amplitude determination model; and the second phase information of the second gradient waveform may be determined by processing the first phase information of the first gradient waveform using the phase determination model.

FIG. 8 is a flowchart illustrating an exemplary process for generating an amplitude determination model according to some embodiments of the present disclosure. In some embodiments, process 800 may be executed by the MRI system 100. For example, the process 800 may be implemented as a set of instructions (e.g., an application) stored in a storage device (e.g., the storage device 150, the storage device 220, and/or the storage 390). In some embodiments, the processing device 120B (e.g., the processor 210 of the computing device 200, the CPU 340 of the mobile device 300, and/or one or more modules illustrated in FIG. 4B) may execute the set of instructions and accordingly be directed to perform the process 800.

In some embodiments, one or more operations of the process 800 may be performed to achieve at least part of operation 520 as described in connection with FIG. 5. In some embodiments, the process 800 may be performed by another device or system other than the MRI system 100, e.g., a device or system of a vendor of a manufacturer. For illustration purposes, the implementation of the process 800 by the processing device 120B is described as an example.

In 810, the processing device 120B (e.g., the acquisition module 405) may obtain a plurality of first training samples. Each of the plurality of first training samples may include sample first amplitude information of a sample first gradient waveform planned to be applied to a sample subject during a sample MRI scan, and ground truth amplitude information of a ground truth gradient waveform applied to the sample subject during the sample MRI scan.

In some embodiments, the sample subject of a first training sample may be of the same type as or a different type from the subject as described in connection with 510. For example, the subject may be the head of a patient, and the sample subject may be the head of another patient or a man-made object (e.g., a phantom). The sample MRI scan may be an actual MRI scan or a simulated MRI scan applied to the sample subject. The sample first gradient waveform of the first training sample refers to a first gradient waveform planned to be applied to the sample subject of the first training sample. For example, the sample first gradient waveform may be defined by sample first amplitude information and sample first phase information. In some embodiments, a plurality of sample MRI scans with different scanning parameters (e.g., a FOV, a bandwidth, a resolution) may be performed on the sample subject, so that a plurality of different sample first gradient waveforms with different shapes may be applied to the sample subject in the sample MRI scans.

The ground truth gradient waveform of the first training sample refers to a measured value of an actual gradient waveform applied to the sample subject in the sample MRI scan. For example, the ground truth gradient waveform may be measured by magnetic field detecting device(s) during the sample MRI scan. As another example, the sample subject may be a water phantom, and the ground truth gradient waveform may be determined based on MRI signals collected during the sample MRI scan of the water phantom. In some embodiments, the ground truth gradient waveform may be defined by ground truth amplitude information and ground truth phase information of the ground truth gradient waveform. The ground truth amplitude information of the ground truth gradient waveform may include an amplitude of the ground truth gradient waveform at each of a plurality of time points during the sample MRI scan. The ground truth phase information of the ground truth gradient waveform may include a phase of the ground truth gradient waveform at each of the plurality of time points during the sample MRI scan.

In some embodiments, a first training sample (or a portion thereof) may be previously generated by a computing device (e.g., the processing device 120B) and stored in a storage device (e.g., the storage device 130, the storage device 220, the storage 390, or an external database). The processing device 120B may retrieve the first training sample (or a portion thereof) from the storage device. Alternatively, the first training sample (or a portion thereof) may be generated by the processing device 120B.

In 820, the processing device 120B (e.g., the acquisition module 405) may obtain a first preliminary model.

In some embodiments, the first preliminary model may be of any type of model (e.g., a machine learning model), for example, a neural network model (e.g., a CNN model, a GAN model), or the like. The first preliminary model may include one or more model parameters. For example, the first preliminary model may be a CNN model and exemplary model parameters of the preliminary model may include the number (or count) of layers, the number (or count) of kernels, a kernel size, a stride, a padding of each convolutional layer, a loss function, or the like, or any combination thereof. Before training, the model parameter(s) of the first preliminary model may have their respective initial values. For example, the processing device 120B may initialize parameter value(s) of the model parameter(s) of the first preliminary model.

In 830, for each of the plurality of first training samples, the processing device 120B (e.g., the training module 406) may generate sample preliminary amplitude information of the sample first gradient waveform of the first training sample using the amplitude response function.

For example, the sample first amplitude information of the sample first gradient waveform may be inputted into the amplitude response function, and the amplitude response function may output the sample preliminary amplitude information. In some embodiments, the generation of the sample preliminary amplitude information may be performed in a similar manner as that of the preliminary amplitude information of the preliminary gradient waveform as described in connection with operation 610, and the descriptions thereof are not repeated here.

In 840, the processing device 120B (e.g., the training module 406) may generate the amplitude determination model by training the first preliminary model using the sample preliminary amplitude information and the ground truth amplitude information of each of the plurality of first training samples.

Figure 9:
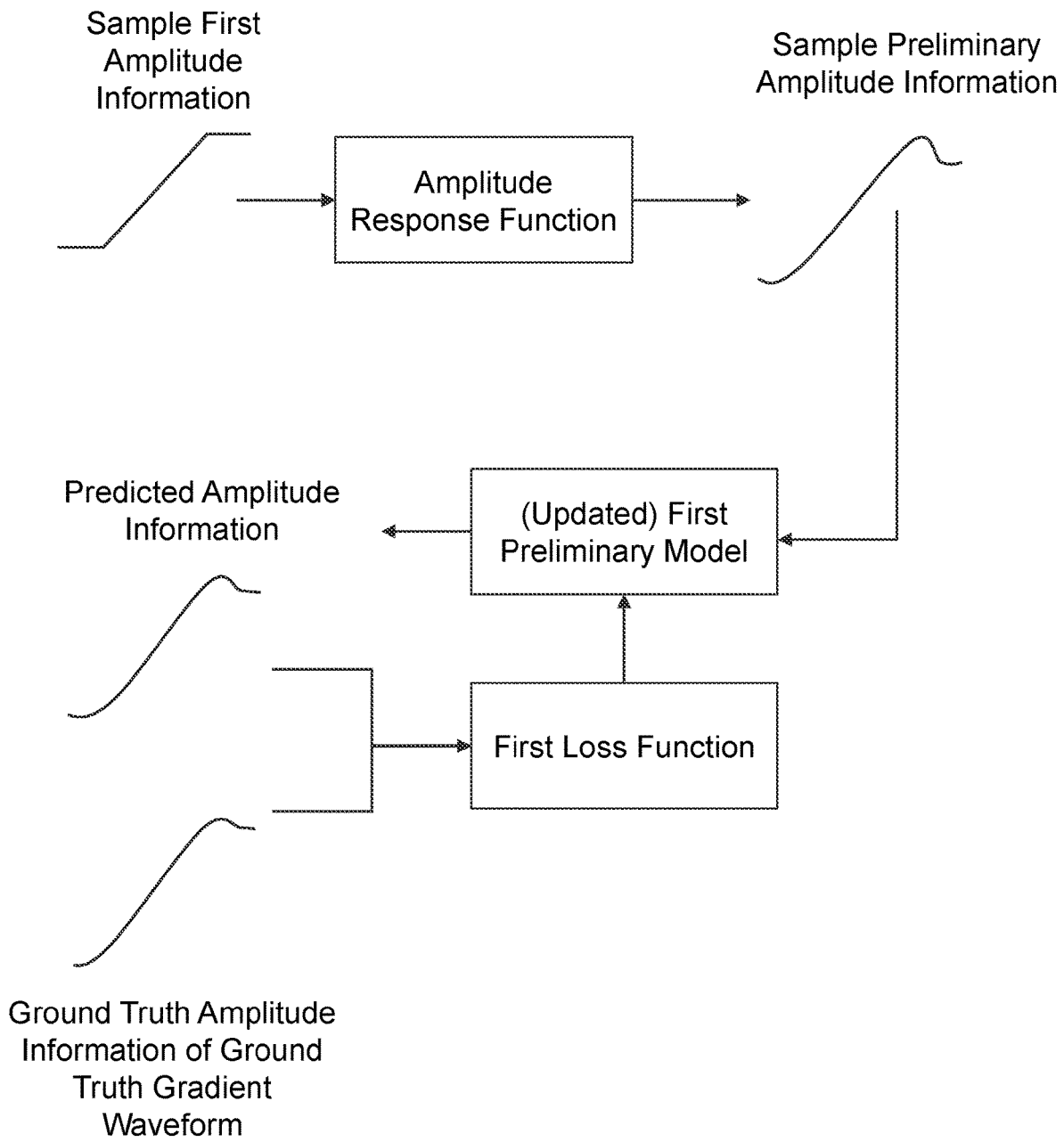
FIG. 9 is a schematic diagram illustrating an exemplary process for generating an amplitude determination model according to some embodiments of the present disclosure.

In some embodiments, the first preliminary model may be trained according to a machine learning algorithm as described elsewhere in this disclosure (e.g., FIG. 5 and the relevant descriptions). For example, the processing device 1206 may generate the amplitude determination model according to a supervised machine learning algorithm by performing one or more iterations to iteratively update the model parameter(s) of the first preliminary model. For illustration purposes, an exemplary current iteration of the iteration(s) is shown in FIG. 9 and described in the following description. The current iteration may be performed based on at least a portion of the first training samples. In some embodiments, a same set or different sets of first training samples may be used in different iterations in training the first preliminary model. For brevity, the first training samples used in the current iteration are referred to as target training samples.

As shown in FIG. 9, for each target training sample, sample preliminary amplitude information may be determined by processing sample first amplitude information of the sample first gradient waveform of the target training sample. In the current iteration, the updated first preliminary model generated in a previous iteration may be evaluated. For example, for each target training sample, the processing device 1206 may determine predicted amplitude information of the ground truth gradient waveform of the target training sample by inputting the sample preliminary amplitude information of the target training sample into the updated first preliminary model. The processing device 1206 may then determine a value of a first loss function of the updated first preliminary model based on the predicted amplitude information and the ground truth amplitude information of the ground truth gradient waveform of each target training sample.

The first loss function may be used to evaluate the accuracy and reliability of the updated first preliminary model, for example, the smaller the first loss function is, the more reliable the updated first preliminary model is. Exemplary first loss functions may include an L1 first loss function, a focal first loss function, a log first loss function, a cross-entropy first loss function, a Dice first loss function, etc. The processing device 1206 may further update the value(s) of the model parameter(s) of the updated first preliminary model to be used in a next iteration based on the value of the loss function according to, for example, a backpropagation algorithm.

In some embodiments, the one or more iterations may be terminated if a termination condition is satisfied in the current iteration. An exemplary termination condition may be that the value of the loss function obtained in the current iteration is less than a predetermined threshold. Other exemplary termination conditions may include that a certain count of iterations is performed, that the loss function converges such that the differences of the values of the loss function obtained in consecutive iterations are within a threshold, etc. If the termination condition is satisfied in the current iteration, the processing device 1206 may designate the updated first preliminary model as the amplitude determination model.

In some embodiments, operation 830 may be omitted, and the amplitude determination model may be generated by training the first preliminary model using the sample first amplitude information and the ground truth amplitude information of each first training sample. For example, during the iteration for generating the amplitude determination model, the predicted amplitude information may be determined based on the sample first amplitude information and the updated first preliminary model.

FIG. 10 is a flowchart illustrating an exemplary process for generating a phase determination model according to some embodiments of the present disclosure. In some embodiments, process 1000 may be executed by the MRI system 100. For example, the process 1000 may be implemented as a set of instructions (e.g., an application) stored in a storage device (e.g., the storage device 150, the storage device 220, and/or the storage 390). In some embodiments, the processing device 120B (e.g., the processor 210 of the computing device 200, the CPU 340 of the mobile device 300, and/or one or more modules illustrated in FIG. 4B) may execute the set of instructions and accordingly be directed to perform the process 1000. In some embodiments, one or more operations of the process 1000 may be performed to achieve at least part of operation 520 as described in connection with FIG. 5.

In 1010, the processing device 120B (e.g., the acquisition module 405) may obtain a plurality of second training samples.

Each of the plurality of second training samples may include sample first phase information of a sample first gradient waveform planned to be applied to a sample subject during a sample MRI scan and ground truth phase information of a ground truth gradient waveform applied to the sample subject during the sample MRI scan. More descriptions regarding the sample subject, the sample first gradient waveform, the sample first phase information, the ground truth gradient waveform, and the ground truth phase information may be found elsewhere in the present disclosure. See, e.g., operation 810 and relevant descriptions thereof.

In 1020, the processing device 120B (e.g., the acquisition module 405) may obtain a second preliminary model.

The second preliminary model may be similar to the first preliminary model as described in connection with operation 820. In some embodiments, the first and second preliminary models may be of the same type or different types of models.

In 1030, for each of the plurality of second training samples, the processing device 120B (e.g., the training module 406) may generate sample preliminary phase information of the sample first gradient waveform of the second training sample using the phase response function.

For example, the sample first phase information of the sample first gradient waveform may be inputted into the phase response function, and the phase response function may output the sample preliminary phase information. In some embodiments, the generation of the sample preliminary phase information may be performed in a similar manner as that of the preliminary phase information of the preliminary gradient waveform as described in connection with operation 610, and the descriptions thereof are not repeated here.

In 1040, the processing device 120B (e.g., the training module 406) may generate the phase determination model by training the second preliminary model using the sample preliminary phase information and the ground truth phase information of each of the plurality of second training samples.

The generation of the phase determination model may be performed in a similar manner as that of the amplitude determination model as described in connection with operation 840. For example, in an iteration for generating the phase determination model, an updated second preliminary model generated in a previous iteration may be evaluated. The updated second preliminary model may be used to determine predicted phase information of a second training sample. The predicted phase information and the ground truth phase information of the second training sample may be used to determine the value of a second loss function relating to the second preliminary model. The second loss function may be similar to the first loss function as described in connection with FIG. 8. The updated second preliminary model may be updated based on the value of the second loss function.

In some embodiments, operation 1030 may be omitted, and the phase determination model may be generated by training the second preliminary model using the sample first phase information and the ground truth phase information of each second training sample. For example, during the iteration for generating the phase determination model, the predicted phase information may be determined based on the sample first phase information and the updated second preliminary model.

FIG. 11 is a flowchart illustrating an exemplary process for jointly generating an amplitude determination model and a phase determination model according to some embodiments of the present disclosure. In some embodiments, process 1100 may be executed by the MRI system 100. For example, the process 1100 may be implemented as a set of instructions (e.g., an application) stored in a storage device (e.g., the storage device 150, the storage device 220, and/or the storage 390). In some embodiments, the processing device 120B (e.g., the processor 210 of the computing device 200, the CPU 340 of the mobile device 300, and/or one or more modules illustrated in FIG. 4B) may execute the set of instructions and accordingly be directed to perform the process 1100. In some embodiments, one or more operations of the process 1100 may be performed to achieve at least part of operation 520 as described in connection with FIG. 5.

In 1110, the processing device 120B (e.g., the acquisition module 405) may obtain a plurality of third training samples.

Each of the plurality of third training samples may include sample first amplitude information and sample first phase information of a sample first gradient waveform planned to be applied to a sample subject during a sample MRI scan, and ground truth amplitude information and ground truth phase information of a ground truth gradient waveform applied to the sample subject during the sample MRI scan. More descriptions regarding the sample subject, the sample first gradient waveform, the sample first amplitude information, the sample first phase information, the ground truth gradient waveform, the ground truth amplitude information, and the ground truth phase information may be found elsewhere in the present disclosure. See, e.g., operation 810 and relevant descriptions thereof.

In 1120, the processing device 120B (e.g., the acquisition module 405) may obtain a third preliminary model comprising a first sub-model and a second sub-model.

In some embodiments, the third preliminary model may be a preliminary hybrid model including the first sub-model and the second sub-model to be trained. The first sub-model may be trained as the amplitude determination model, and the second sub-model may be trained as the phase determination model. In some embodiments, the first and second sub-models may be of the same type or different types of models. In some embodiments, the first sub-model may be similar to the first preliminary model as described in connection with operation 820, and the second sub-model may be similar to the second preliminary model as described in connection with operation 1020.

In 1130, the processing device 120B (e.g., the acquisition module 405) may generate a trained hybrid model by training the third preliminary model using the plurality of third training samples.

The generation of the trained hybrid model may be performed in a similar manner as that of the amplitude determination model as described in connection with operation 840. For example, in an iteration for generating the trained hybrid model, an updated third preliminary model generated in a previous iteration may be evaluated. The updated third preliminary model may be used to determine predicted phase information and predicted amplitude information of a third training sample. The predicted phase information, the predicted amplitude information, the ground truth phase information, and the ground truth phase information of the third training sample may be used to determine the value of a third loss function relating to the third preliminary model. The third loss function may be similar to the first loss function as described in connection with FIG. 8. The updated third preliminary model may be updated based on the value of the third loss function. In some embodiments, the third loss function may include a first component for measuring a difference between the ground truth amplitude information and the predicted amplitude information, and a second component for measuring a difference between the ground truth phase information and the predicted phase information. The first component may be used to update the first sub-model of the updated third preliminary model, and the second component may be used to update the second sub-model of the updated third preliminary model.

In 1140, the processing device 120B (e.g., the training module 406) may designate the trained first sub-model of the trained hybrid model as the amplitude determination model.

In 1150, the processing device 120B (e.g., the training module 406) may designate the trained second sub-model of the trained hybrid model as the phase determination model.

It should be noted that the above descriptions regarding FIGS. 8-11 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 800 may be accomplished with one or more additional operations not described and/or without one or more of the operations discussed above.

For example, after a trained model (the amplitude determination model, the phase determination model, the trained hybrid model) is generated, the processing device 1206 may further test the trained model using a set of testing samples. As another example, the processing device 1206 may update the trained model periodically or irregularly based on one or more newly-generated training samples (e.g., new sample first gradient waveform in MRI scan). As yet another example, a training sample (or a portion thereof) may be preprocessed before model training. Merely by way of example, one or more waveform signal processing operations (e.g., linearization, denoising, filtering, sharpen, etc.) may be performed on a sample first gradient waveform. As still another example, before operation 1130, the processing device 1206 may determine sample preliminary amplitude information and sample preliminary phase information of each third training sample, and train the third preliminary model using the sample preliminary amplitude information, the sample preliminary phase information, the ground truth amplitude information, and the ground truth phase information of each third training sample.

FIG. 12 is a flowchart illustrating an exemplary process for performing an MRI scan on a subject according to some embodiments of the present disclosure. In some embodiments, process 1200 may be executed by the MRI system 100. For example, the process 1200 may be implemented as a set of instructions (e.g., an application) stored in a storage device (e.g., the storage device 150, the storage device 220, and/or the storage 390). In some embodiments, the processing device 120A (e.g., the processor 210 of the computing device 200, the CPU 340 of the mobile device 300, and/or one or more modules illustrated in FIG. 4A) may execute the set of instructions and accordingly be directed to perform the process 1200. The operations of the illustrated process presented below are intended to be illustrative. In some embodiments, the process 1200 may be accomplished with one or more additional operations not described and/or without one or more of the operations discussed. Additionally, the order of the operations of process 1200 illustrated in FIG. 12 and described below is not intended to be limiting.

In 1210, the processing device 120A (e.g., the acquisition module 401) may obtain a first gradient waveform planned to be applied to a subject. For example, the processing device 120A may obtain first amplitude information and first phase information of the first gradient waveform. More descriptions regarding the first gradient waveform may be found elsewhere in the present disclosure. See, e.g., operation 510 and relevant descriptions thereof.

In 1220, the processing device 120A (e.g., the determination module 402) may determine a second gradient waveform based on the first gradient waveform and a gradient waveform determination model, wherein the gradient waveform determination model may have been trained according to a machine learning algorithm.

The second gradient waveform may be regarded as an estimated value of an actual gradient waveform that will be actually applied to the subject during the MRI scan when the MRI scan is performed according to the first gradient waveform. Operation 1220 may be performed in a similar manner as operation 520 as described in connection with FIG. 5, and the descriptions thereof are not repeated here.

In 1230, the processing device 120A (e.g., the control module 404) may direct an MRI scanner to perform the MRI scan on the subject based on the second gradient waveform.

In some embodiments, the processing device 120A may determine one or more scanning parameters to achieve the second gradient waveform, and direct the MRI scanner to perform the MRI scan on the subject based on the one or more scanning parameters.

In some embodiments, the processing device 120A (e.g., the determination module 404) may determine an adjusted gradient waveform by adjusting the first gradient waveform according to the second gradient waveform. Further, the processing device 120A (e.g., the control module 404) may direct the MRI scanner to perform the MRI scan on the subject according to the adjusted gradient waveform.

As aforementioned, due to hardware limitations, an actual gradient waveform applied to the subject during the MRI scan is usually different from the ideal first gradient waveform. The processing device 120A may determine the adjusted gradient waveform according to the second gradient waveform (i.e., an estimated actual gradient waveform when the MRI scan is performed according to the first gradient waveform), such that when the MRI scan is performed according to the adjusted gradient waveform, an actual gradient waveform applied to the subject under the effect of the hardware limitations may be as close to the first gradient waveform as possible.

For example, by comparing the first gradient waveform and the second gradient waveform, the processing device 120A may determine a rule reflecting how the hardware limitations will affect the application of the first gradient waveform, and adjust the first gradient waveform based on the rule. Merely by way of example, if the rule indicates that the second gradient waveform drops rapidly in a period while the first gradient waveform is in a stable state in the period, the processing device 120A may adjust the portion of the first gradient waveform in the period to increase. In such cases, when the MRI scan is performed according to the adjusted gradient waveform, an actual gradient waveform may be close to the first gradient waveform even if the adjusted portion drops due to hardware limitations in the period.

By determining the adjusted gradient waveform based on the second gradient waveform and performing the MRI scan according to the adjusted gradient waveform, the actual gradient waveform applied to the subject during the MRI scan may be close to the ideal first gradient waveform, which may achieve a desired scan effect. In some embodiments, the MRI scan may be an ultrashort echo-time MRI or a spiral MRI scan. In some embodiments, the processing device 120A may further generate a target reconstruction image of the subject based on scan data collected in the MRI scan and the first gradient waveform. As described in connection with operation 1230, an actual gradient waveform applied to the subject during the subject may be close to the first gradient waveform when the MRI scan is performed according to the first gradient waveform. Reconstructing the target reconstruction image based on the first gradient waveform may improve the reconstruction accuracy.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
  at least one storage device including a set of instructions for generating a gradient waveform determination model; and
  at least one processor configured to communicate with the at least one storage device, wherein when executing the set of instructions, the at least one processor is configured to direct the system to perform operations including:
  obtaining a plurality of training samples;
  obtaining a preliminary model; and
  generating the gradient waveform determination model by training the preliminary model using the training samples, wherein each of the plurality of training samples includes:
    sample information of a sample gradient waveform planned to be applied to a sample subject during a sample MRI scan; and
    ground truth information of a ground truth gradient waveform applied to the sample subject during the sample MRI scan.

2. The system of claim 1, wherein the operations further include:
  obtaining MRI scan data of a subject by directing an MRI scanner to perform an MRI scan on the subject according to a first gradient waveform;
  determining, based on the first gradient waveform and the gradient waveform determination model, a second gradient waveform; and
  generating, based on the second gradient waveform and the MRI scan data, a target reconstruction image of the subject.

3. The system of claim 2, wherein the determining, based on the first gradient waveform and the gradient waveform determination model, a second gradient waveform comprises:
  determining a preliminary gradient waveform by processing the first gradient waveform using at least one response function; and
  determining the second gradient waveform based on the preliminary gradient waveform and the gradient waveform determination model.

4. The system of claim 3, wherein the at least one response function includes an amplitude response function and a phase response function, and
  the determining a preliminary gradient waveform by processing the first gradient waveform using at least one response function comprises:
    determining preliminary amplitude information of the preliminary gradient waveform by processing first amplitude information of the first gradient waveform using the amplitude response function; and
    determining preliminary phase information of the preliminary gradient waveform by processing first phase information of the first gradient waveform using the phase response function.

5. The system of claim 4, wherein the gradient waveform determination model comprises an amplitude determination model and a phase determination model, and
  the determining the second gradient waveform MRI based on the preliminary gradient waveform and the gradient waveform determination model comprises:
    determining second amplitude information of the second gradient waveform by processing the preliminary amplitude information using the amplitude determination model; and
    determining second phase information of the second gradient waveform by processing the preliminary amplitude information using the phase determination model.

6. The system of claim 1, wherein the operations further include:
obtaining a first gradient waveform planned to be applied to a subject during an MRI scan;
determining, based on the first gradient waveform and the gradient waveform determination model, a second gradient waveform; and
directing, based on the second gradient waveform, an MRI scanner to perform the MRI scan on the subject.

7. The system of claim 6, wherein the directing, based on the second gradient waveform, an MRI scanner to perform the MRI scan on the subject comprises:
determining an adjusted gradient waveform by adjusting the first gradient waveform according to the second gradient waveform; and
directing the MRI scanner to perform the MRI scan on the subject according to the adjusted gradient waveform.

8. The system of claim 6, wherein the determining, based on the first gradient waveform and the gradient waveform determination model, a second gradient waveform comprises:
determining a preliminary gradient waveform by processing the first gradient waveform using at least one response function; and
determining the second gradient waveform based on the preliminary gradient waveform and the gradient waveform determination model.

9. The system of claim 8, wherein the at least one response function includes an amplitude response function and a phase response function, and
the determining a preliminary gradient waveform by processing the first gradient waveform using at least one response function comprises:
determining preliminary amplitude information of the preliminary gradient waveform by processing first amplitude information of the first gradient waveform using the amplitude response function; and
determining preliminary phase information of the preliminary gradient waveform by processing first phase information of the first gradient waveform using the phase response function.

10. The system of claim 9, wherein the gradient waveform determination model comprises an amplitude determination model and a phase determination model, and
the determining the second gradient waveform MRI based on the preliminary gradient waveform and the gradient waveform determination model comprises:
determining second amplitude information of the second gradient waveform by processing the preliminary amplitude information using the amplitude determination model; and
determining second phase information of the second gradient waveform by processing the preliminary amplitude information using the phase determination model.

11. The system of claim 1, wherein:
the gradient waveform determination model includes an amplitude determination model,
the sample information of the sample gradient waveform includes sample amplitude information of the sample gradient waveform, and
the ground truth information of the ground truth gradient waveform includes ground truth amplitude information of the ground truth gradient waveform.

12. The system of claim 11, wherein the generating the gradient waveform determination model by training the preliminary model using the training samples comprises:
for each of the plurality of training samples, generating sample preliminary amplitude information of the sample gradient waveform of the training sample using an amplitude response function; and
generating the amplitude determination model by training the preliminary model using the sample preliminary amplitude information and the ground truth amplitude information of each of the plurality of training samples.

13. The system of claim 1, wherein:
the gradient waveform determination model includes a phase determination model,
the sample information of the sample gradient waveform includes sample phase information of the sample gradient waveform, and
the ground truth information of the ground truth gradient waveform includes ground truth phase information of the ground truth gradient waveform.

14. The system of claim 13, wherein the generating the gradient waveform determination model by training the preliminary model using the training samples comprises:
for each of the plurality of training samples, generating sample preliminary phase information of the sample gradient waveform of the training sample using a phase response function; and
generating the phase determination model by training the preliminary model using the sample preliminary phase information and the ground truth phase information of each of the plurality of training samples.

15. The system of claim 1, wherein:
the gradient waveform determination model includes an amplitude determination model and a phase determination model that are jointly trained,
the preliminary model is a hybrid model including a first sub-model and a second sub-model,
the sample information of the sample gradient waveform includes sample amplitude information and sample phase information of the sample gradient waveform,
the ground truth information of the ground truth gradient waveform includes ground truth amplitude information and ground truth phase information of the ground truth gradient waveform, and
the generating the gradient waveform determination model by training the preliminary model using the training samples comprises:
generating a trained hybrid model by training the preliminary model using the training samples; and
designating the trained first sub-model and the trained second sub-model of the trained hybrid model as the amplitude determination model and the phase determination model, respectively.

16. The system of claim 15, wherein the amplitude determination model and the phase determination model are convolutional neural network models.

17. The system of claim 1, wherein the MRI scan is an ultrashort echo-time MRI scan or a spiral MRI scan.

18. A method for generating a gradient waveform determination model implemented on a computing device having at least one processor and at least one storage device, the method comprising:
obtaining a plurality of training samples;
obtaining a preliminary model; and
generating the gradient waveform determination model by training the preliminary model using the training samples, wherein each of the plurality of training samples includes:

sample information of a sample gradient waveform planned to be applied to a sample subject during a sample MRI scan; and ground truth information of a ground truth gradient waveform applied to the sample subject during the sample MRI scan.

19. The method of claim 18, wherein the method further includes:

obtaining MRI scan data of a subject by directing an MRI scanner to perform an MRI scan on the subject according to a first gradient waveform;

determining, based on the first gradient waveform and the gradient waveform determination model, a second gradient waveform; and generating, based on the second gradient waveform and the MRI scan data, a target reconstruction image of the subject.

20. A non-transitory computer readable medium, comprising a set of instructions for generating a gradient waveform determination model, wherein when executed by at least one processor, the set of instructions direct the at least one processor to effectuate a method, the method comprising:

obtaining a plurality of training samples;

obtaining a preliminary model; and generating the gradient waveform determination model by training the preliminary model using the training samples, wherein each of the plurality of training samples includes:

sample information of a sample gradient waveform planned to be applied to a sample subject during a sample MRI scan; and ground truth information of a ground truth gradient waveform applied to the sample subject during the sample MRI scan.

* * * * *